US010925811B2

(12) United States Patent  (10) Patent No.: US 10,925,811 B2
Bringley et al.  (45) Date of Patent: Feb. 23, 2021

(54) POROUS COMPOSITE FILLER COMPOSITIONS

(71) Applicants: Kerr Corporation, Orange, CA (US); Transparent Materials, LLC, Rochester, NY (US)

(72) Inventors: Joseph F Bringley, Rochester, NY (US); Patrick M Lambert, Rochester, NY (US); Weijie Huang, Irvine, CA (US)

(73) Assignees: Kerr Corporation, Brea, CA (US); Transparent Materials, LLC, Rochester, NY (US)

( * ) Notice: Subject to any disclaimer, the term of this patent is extended or adjusted under 35 U.S.C. 154(b) by 38 days.

(21) Appl. No.: 15/462,836

(22) Filed: Mar. 18, 2017

(65) Prior Publication Data

US 2018/0263861 A1  Sep. 20, 2018

(51) Int. Cl.
| | |
|---|---|
| A61K 6/76 | (2020.01) |
| C08K 3/36 | (2006.01) |
| C08K 3/22 | (2006.01) |
| C09C 1/00 | (2006.01) |
| C09C 1/30 | (2006.01) |
| A61K 6/887 | (2020.01) |

(52) U.S. Cl.
CPC .............. *A61K 6/76* (2020.01); *A61K 6/887* (2020.01); *C08K 3/22* (2013.01); *C08K 3/36* (2013.01); *C09C 1/0081* (2013.01); *C09C 1/309* (2013.01); *C09C 1/3018* (2013.01); *C09C 1/3072* (2013.01); *C09C 1/3081* (2013.01); *C01P 2002/60* (2013.01); *C01P 2004/61* (2013.01); *C01P 2004/64* (2013.01); *C01P 2006/60* (2013.01); *C08K 2003/2244* (2013.01); *C08K 2201/003* (2013.01)

(58) Field of Classification Search
None
See application file for complete search history.

(56) References Cited

U.S. PATENT DOCUMENTS 4,217,264 A * 8/1980 Mabie ................ A61K 6/083
  106/35
4,306,913 A * 12/1981 Mabie ................ A61K 6/083
  106/35

(Continued)

FOREIGN PATENT DOCUMENTS

EP  0 983 762  8/2013
EP  3072498 A1 * 9/2016 .......... A61K 6/0017

(Continued)

*Primary Examiner* — Peter A Salamon
(74) *Attorney, Agent, or Firm* — Sheppard, Mullin, Richter & Hampton LLP

(57) ABSTRACT

A composite filler comprising thermally processed porous inorganic mixed particles of silica and at least one heteroparticle selected from the group consisting of zirconia, hafnia, or yttria and a polymer occupying the pores of the porous inorganic mixed particles, wherein the porous inorganic mixed particles are thermally processed at a temperature of from 650 to 900° C., as well as a dental restorative comprising a resin and a composite filler, and optionally other fillers, wherein said resin has a refractive index that increases upon curing, and wherein the opacities of the both uncured and cured restorative are less than 45.

17 Claims, 1 Drawing Sheet

Table 1. Comparison Example 1 and Examples 2 - 12.

| Composite Filler Properties | | C1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 |
|---|---|---|---|---|---|---|---|---|---|---|---|---|---|
| Silica 1° particle diameter (nm) | | 20 | 20 | 20 | 20 | 20 | 80 | 80 | 80 | 20 & 80* | 20 & 80* | 20 & 80* | 20 |
| Firing Temperature, °C | | 966 | 966 | 866 | 966 | 866 | 766 | 816 | 866 | 766 | 816 | 866 | 866 |
| RI** porous inorganic particles | | 1.523 | 1.523 | 1.523 | 1.523 | 1.523 | 1.523 | 1.523 | 1.523 | 1.523 | 1.523 | 1.523 | 1.523 |
| RI** polymerized organic portion (resin) | | 1.532 | 1.532 | 1.532 | 1.532 | 1.532 | 1.532 | 1.532 | 1.532 | 1.532 | 1.532 | 1.532 | 1.550 |
| Polymer Weight Percent | | 14.2 | 14.2 | 14.2 | 9.1 | 9.1 | 11.9 | 11.9 | 11.9 | 11.9 | 11.9 | 11.9 | 14.2 |
| 2° particle diameter (microns) | | 6.0 | 4.0 | 2.6 | 2.6 | 3.2 | 4.3 | 4.8 | 4.6 | 3.8 | 3.8 | 3.8 | 2.9 |
| Composite Properties | | | | | | | | | | | | | |
| Wt. % fumed silica | | 2 | 2 | 2 | 2 | 2 | 2 | 2 | 2 | 2 | 2 | 2 | 2 |
| Wt. % Composite Filler | | 70 | 70 | 70 | 70 | 70 | 70 | 70 | 70 | 70 | 70 | 70 | 70 |
| Wt. % Resin 1 | | 28 | 28 | 28 | 28 | 28 | - | - | - | - | - | - | 28 |
| Wt. % Resin 2 | | - | - | - | - | - | 28 | 28 | 28 | 28 | 28 | 28 | |
| Gloss retention (initial) | | 51.8 | 90.3 | 90.6 | 90 | 89.3 | 89.1 | 84.9 | 82.5 | 88.0 | 87.2 | 89.8 | 89.8 |
| Gloss retention (after 1 h) | | 45.8 | 54.2 | 73.7 | 50.8 | 61.9 | 83.1 | 81.2 | 79.7 | 80.7 | 78.1 | 71.2 | 71.2 |
| Gloss retention (after 4 h) | | 45.3 | 57.5 | 74.8 | 59.9 | 70.3 | 82.7 | 80.9 | 82.1 | 78.6 | 79.7 | 70.9 | 70.9 |
| Flexural Strength (MPa) | | NA | 119.7 | 127.7 | 123.0 | 126.1 | 122 | 126 | 131 | 131 | 110 | 111 | 111 |
| Flexural Modulus (MPa) | | NA | 9140 | 8400 | 10400 | 10400 | 8900 | 8620 | 8810 | 9360 | 8490 | 8650 | 8650 |
| Opacity (before cure) | | 34.5 | | 24.4 | | | | | | | | | 27.8 |
| Opacity (after cure) | | 52.6 | | 51.0 | | | | | | | | | 38.9 |

*Silica primary particles were chosen from Nalco 2327 and Nalco 2329 at a 50:50 weight ratio.   ** RI = refractive index

(56) References Cited

U.S. PATENT DOCUMENTS

| | | | | |
|---|---|---|---|---|
| 4,503,169 A * | 3/1985 | Randklev | ............... | A61K 6/083 |
| | | | | 106/35 |
| 5,356,951 A * | 10/1994 | Yearn | ..................... | A61K 6/083 |
| | | | | 523/115 |
| 7,091,258 B2 * | 8/2006 | Neubert | ............... | A61K 6/0091 |
| | | | | 433/212.1 |
| 7,541,017 B2 * | 6/2009 | Bringley | .............. | B01J 13/0008 |
| | | | | 424/1.29 |
| 8,287,952 B2 * | 10/2012 | Bringley | .............. | B01J 13/0008 |
| | | | | 424/489 |
| 8,617,306 B2 * | 12/2013 | Lambert | ............... | C04B 14/041 |
| | | | | 106/481 |
| 8,946,318 B2 * | 2/2015 | Akizumi | .............. | A61K 6/0058 |
| | | | | 523/115 |
| 9,017,733 B2 * | 4/2015 | Bringley | ............... | A61L 27/427 |
| | | | | 424/691 |
| 9,862,813 B2 * | 1/2018 | Bringley | ................ | A61K 6/027 |
| 10,004,667 B2 * | 6/2018 | Yamazaki | .............. | A61K 6/083 |
| 2013/0005846 A1 * | 1/2013 | Yamazaki | ............ | A61K 6/0073 |
| | | | | 521/149 |
| 2016/0222193 A1 * | 8/2016 | Bringley | ................ | A61K 6/027 |
| 2018/0263861 A1 * | 9/2018 | Bringley | .............. | A61K 6/0088 |

FOREIGN PATENT DOCUMENTS

| | | | | |
|---|---|---|---|---|
| WO | WO2012/002996 | | 1/2012 | |
| WO | WO2015034881 | | 3/2015 | |
| WO | WO-2015034881 A1 * | 3/2015 | ............. | A61K 6/027 |

\* cited by examiner

Table 1. Comparison Example 1 and Examples 2 - 12.

| Composite Filler Properties | C1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 |
|---|---|---|---|---|---|---|---|---|---|---|---|---|
| Silica 1° particle diameter (nm) | 20 | 20 | 20 | 20 | 20 | 80 | 80 | 80 | 20 & 80* | 20 & 80* | 20 & 80* | 20 |
| Firing Temperature, °C | 966 | 966 | 866 | 966 | 866 | 766 | 816 | 866 | 766 | 816 | 866 | 866 |
| RI** porous inorganic particles | 1.523 | 1.523 | 1.523 | 1.523 | 1.523 | 1.523 | 1.523 | 1.523 | 1.523 | 1.523 | 1.523 | 1.523 |
| RI** polymerized organic portion (resin) | 1.532 | 1.532 | 1.532 | 1.532 | 1.532 | 1.532 | 1.532 | 1.532 | 1.532 | 1.532 | 1.532 | 1.550 |
| Polymer Weight Percent | 14.2 | 14.2 | 14.2 | 9.1 | 9.1 | 11.9 | 11.9 | 11.9 | 11.9 | 11.9 | 11.9 | 14.2 |
| 2° particle diameter (microns) | 6.0 | 4.0 | 2.6 | 2.6 | 3.2 | 4.3 | 4.8 | 4.6 | 3.8 | 3.8 | 3.8 | 2.9 |
| Composite Properties | | | | | | | | | | | | |
| Wt. % fumed silica | 2 | 2 | 2 | 2 | 2 | 2 | 2 | 2 | 2 | 2 | 2 | 2 |
| Wt. % Composite Filler | 70 | 70 | 70 | 70 | 70 | 70 | 70 | 70 | 70 | 70 | 70 | 70 |
| Wt. % Resin 1 | 28 | 28 | 28 | 28 | 28 | - | - | - | - | - | - | 28 |
| Wt. % Resin 2 | - | - | - | - | - | 28 | 28 | 28 | 28 | 28 | 28 | |
| Gloss retention (initial) | 51.8 | 90.3 | 90.6 | 90 | 89.3 | 89.1 | 84.9 | 82.5 | 88.0 | 87.2 | 89.8 | 89.8 |
| Gloss retention (after 1 h) | 45.8 | 54.2 | 73.7 | 50.8 | 61.9 | 83.1 | 81.2 | 79.7 | 80.7 | 78.1 | 71.2 | 71.2 |
| Gloss retention (after 4 h) | 45.3 | 57.5 | 74.8 | 59.9 | 70.3 | 82.7 | 80.9 | 82.1 | 78.6 | 79.7 | 70.9 | 70.9 |
| Flexural Strength (MPa) | NA | 119.7 | 127.7 | 123.0 | 126.1 | 122 | 126 | 131 | 131 | 110 | 111 | 111 |
| Flexural Modulus (MPa) | NA | 9140 | 8400 | 10400 | 10400 | 8900 | 8620 | 8810 | 9360 | 8490 | 8650 | 8650 |
| Opacity (before cure) | 34.5 | | 24.4 | | | | | | | | | 27.8 |
| Opacity (after cure) | 52.6 | | 51.0 | | | | | | | | | 38.9 |

*Silica primary particles were chosen from Nalco 2327 and Nalco 2329 at a 50:50 weight ratio.    ** RI = refractive index

POROUS COMPOSITE FILLER COMPOSITIONS

FIELD OF THE INVENTION

The present invention relates to polymeric composites comprising inorganic fillers and organic, or organometallic, polymers. The invention relates to filler compositions that are used in the preparation of inorganic-organic polymeric composites, and, in particular, light curable composites. Still further, the invention relates to composite fillers that are used in dental applications, such as tooth restorations, for example, cavity fillings, adhesive compositions, veneers, crowns, bridges and teeth replacements.

BACKGROUND OF THE INVENTION

Inorganic-organic polymer composite materials are used in a wide variety of applications including structural materials, high performance composites, optical components, aerospace, biomedical implants and dental applications. Generally, composites are employed where performance requirements are demanding and not easily fulfilled with traditional structural materials. For example, inorganic materials, such as glass, ceramic and stone, are very hard, scratch resistant and even sometimes transparent (e.g., glass), but suffer from the fact that they are very heavy and brittle. Polymers, conversely, are light and durable, but have poor hardness, abrasion and wear resistance. Composites, made from the combination of inorganic materials and polymers, may have properties that lie in between, providing materials that are simultaneously strong but lightweight, hard but flexible, abrasion resistant and durable.

In order to achieve such properties, in practice, hard inorganic materials are mixed into polymers, or polymer precursors, monomers and/or oligomers, referred to as resins, and the mixture is then cured to form a composite. Hereafter, inorganic addenda are referred to as performance additives. Performance additives are an extremely important component of coatings and composite formulations. They impart a wide variety of properties to the end products including strength and toughness, scratch and mar resistance, UV absorption, optical properties, anticorrosion, and biocompatibility (for medical based coatings). Typical performance addenda are comprised of inorganic metal oxides, such as silica, titania, alumina, and zinc oxide; they may be categorized according to their size: micron-sized (0.2-100 μm) or nano-sized (1-200 nm).

There are several problems or difficulties generally experienced in mixing performance additives into polymers. First, polymers or polymer precursors may be viscous and the addition of performance materials only increases the viscosity and limits the loading of material that may be achieved, and creates difficulty in handling, molding and crafting the composite into an article of commerce. Second, inorganic performance materials generally have a high surface energy compared to resins, and the mismatch in the interfacial energy may cause the inorganic materials to agglomerate and/or aggregate, making a homogeneous dispersion difficult or impossible to achieve. This problem is particularly acute if the particle size of the performance additive is small, especially in the case of nanomaterials, i.e., materials with a particle size between 1 to 200 nm.

The polymer industry is transforming from composites that are polymerized, or cured, using heat (thermal set polymers) to those that are cured using ultraviolet or visible light, or low energy electrons (UVEB). UVEB curable resins offer tremendous energy and waste savings to the coatings and composites industries because they are polymerized (cured) directly with light and also because they generally do not contain volatile diluents, such as solvents or carriers that may be considered hazardous air pollutants. UVEB curing is far more energy efficient, since it overcomes the thermal loss that is prevalent in conventional thermoset coating systems. Ironically, the fundamental advantages of UVEB systems, where a solventless medium is cured rapidly by radiation, are also the source of significant system limitations.

Light curing requires that the coating and/or object must be sufficiently transparent in the spectral region of curing, since the penetration depth and absorption of the curing radiation is essential to achieve rapid and efficient curing. This limits the performance additives (fillers, stabilizers, functional additives, and coating aids) that can be added to UVEB systems, since the additives must also fulfill the requirement of being optically transparent in the curing region of the spectrum. While there are some types of addenda that meet this requirement, their formulation into UVEB resins can be very difficult, since these systems do not contain diluents or volatile components.

Diluents (solvents and volatiles) act as dispersion aids and carriers that enable integration of a wide variety of functional additives into paints and coatings formulations. Diluents give the formulator tools with which to adjust viscosity and rheology, disperse solids and overcome formulation incompatibilities. These factors, in combination with the absorption requirements of UVEB formulations, greatly limit the performance additives that can be utilized.

The dental industry, primarily due to health concerns, is rapidly transitioning dental restoratives (e.g., cavity fillings, dental restorations) from the conventional mercury-based amalgams to highly filled, light curable, polymer-based composites. Polymer-based composites are safer and better match the color and appearance of human tooth enamel, but are often softer, not as strong or as durable as the traditional metal amalgams. To resolve these problems, manufacturers have developed microfilled polymer composites that have strength, hardness and durability close to that of the conventional amalgams. To achieve the performance requirements, polymers are highly filled at loadings of 70-80% by weight performance additives. It is generally desirable that the filling percentage be as high as possible to approximate the hardness of teeth, however, loadings greater than about 80% are very difficult to achieve.

From the patient's perspective, the aesthetic quality of the restoration is extremely important, since teeth are an important part of personal appearance. Matching the aesthetic quality of natural human enamel is difficult, since teeth, although opaque, have a translucent or opalescent quality that provides luster and visual brilliance. To achieve these qualities, some dental restorative manufacturers have developed performance additives that are closely matched in refractive index to the polymers used to prepare dental restoratives. The more closely index-matched the performance additives are to the polymer, the greater the translucency and aesthetic quality of the restoration. Because the two materials have the same index of refraction, there is little scatter of light and the resulting restorative composite resembles natural teeth in optical translucency and appearance. This also has the added benefit that it increases light penetration and the curing depth of the composite.

There are two types of fillers that are used in dentistry to give high optical translucency and aesthetic quality. The first is a glass or melt derived filler that is produced by melting a glass composition of known refractive index, rapidly cooling or quenching the melt (for example into cold water) into a glass, and then pulverizing the glass to a given particle size, usually between about 0.4 and 10.0 microns. This process produces amorphous, shard-like particles of low surface area, usually between about 1-10 $m^2/g$. A prevalent example of this type of filler is barium glass.

The second is a microporous filler that is produced from the thermal treatment of mixtures of colloidal dispersions of oxides, such as silica, zirconia and alumina. The refractive index is controlled through control of the composition. This process was first developed by Mabie et al., U.S. Pat. Nos. 4,217,264 and 4,306,913, to produce amorphous, microporous mixed oxides of silica and zirconia, and later by Randklev U.S. Pat. No. 4,503,169 to produce crystalline, microporous mixed oxides of silica, zirconia, and other oxides.

The microporous fillers are highly fused materials consisting of silica and other oxide particles and, because they are processed at a temperature below the melting temperature of any of the components, they are porous and have a high surface area. As Randklev pointed out, the surface area may be as high as 200 $m^2/g$ and the average pore volume may be as high as 40% of the volume of the filler. These microporous fillers have received much attention because of their numerous advantages, including improved finish, gloss, strength, and abrasion resistance.

There is a problem, however, in that for microporous fillers, both the internal porosity and surface area is high, and it is difficult to achieve high loadings of the porous fillers in dental monomers. The internal pores soak up the organic resin, limiting the fraction of resin that may keep the suspension in a fluid state, and the viscosity rises exponentially making the paste unworkable.

There is an additional problem with modern dental composite restorations. Modern dental materials contain a liquid, polymerizable resin in the form of monomers, or monomer mixtures, as an essential component. It is known that, during polymerization, a volume contraction takes place. The volume contraction is often called shrinkage and is attributable to the development of covalent bonds between the monomer molecules during polymerization, whereby the distance between the molecules is decreased. During the preparation of pre-shaped parts, the polymerization shrinkage has a very disadvantageous effect on the dimensional stability and the mechanical properties of the molded bodies. In the case of adhesives and gluing compounds, the polymerization shrinkage adversely affects the adhesion properties and the bonding strength, which deteriorates the adhesion between restoration material and the natural tooth substance of dental materials. Voids and cracks may result which become reservoirs for bacteria and encourage the development of secondary caries.

In order to reduce the polymerization shrinkage of dental materials, the industry has developed pre-polymerized fillers in which a mixture of inorganic fillers and monomers is polymerized and then ground to the desired size and then mixed again with monomers to form a flowable mixture that can be molded in tooth restorations. Because a portion of the polymer is pre-polymerized, the amount of shrinkage is slightly reduced. The preparation and use of such fillers, sometimes called pre-polymers or composite fillers, has been described in the patent and scientific literature.

In the application of composites in dentistry, the greatest problem arises from simultaneously achieving all of the required (or desired) properties of a dental composite. Ideally, a dental composite should have good viscosity and handling before cure so that the dentist may sculpt a restoration matching the adjacent natural teeth. It should have high transparency before cure so that the curing-light may penetrate deeply into the composite. After cure, the composite should have high mechanical strength, low volume shrinkage, good translucency (optical properties like that of teeth) and high-gloss and abrasion resistance (for aesthetic longevity). In practice, it is exceedingly difficult for the formulator of dental composites to achieve, simultaneously, all of these properties, since many are counter-opposed. For example, large particles generally afford dental composites with low-viscosity and high-mechanical strength, but unfortunately poor gloss and abrasion resistance, and the exact opposite is true for smaller particles.

U.S. Pat. No. 5,356,951 to Yearn et al. discloses a composition for dental restorative material comprising: (a) a first methacrylate or acrylate monomer having at least one unsaturated double bond, (b) (i) a composite filler obtained by curing and pulverizing a mixture of a first glass powder component having a maximum particle diameter of 10 µm or less and a mean particle diameter of 0.1 to 5 µm with a second methacrylate or acrylate monomer having at least one unsaturated double bond, (ii) a second glass powder component having a maximum particle diameter of 10 µm or less and a mean particle diameter of 0.1 to 5 µm, and iii) a fine particle filler having a mean particle diameter of 0.01 to 0.04 µm, and a photo-polymerization initiator. The filler described is a non-porous filler.

U.S. Pat. No. 7,091,258 to Neubert et al. discloses a composition comprising: (i) 10 to 80 wt. % organic binder; (ii) 0.01 to 5 wt. % polymerization initiator; (iii) 20 to 90 wt. % particulate composite filler, comprising a polymerized mixture of organic binder and inorganic filler, the composite filler particles having an average particle size of 20 to 50 µm, each wt. % of (i), (ii), and (iii) relative to the total mass of the composition; and wherein the composition contains at most 10 wt. % composite filler particles having a size of <10 µm, relative to the total mass of the particulate composite filler in the composition. There is a problem, however, in that the material of Nuebert et al. requires extensive grinding in order to be used as a dental filler, and, at best, a relatively large particle size (20-50 µm) is achieved.

EP 0 983 762 A1 to Katsu discloses an organic-inorganic composite filler for use in dentistry. The composite filler is prepared by curing a mixture of a particulate filler with an average particle size of 20 nm or less and a methacrylate or acrylate monomer with a viscosity of 60 cP or more and pulverizing the cured mixture. The materials are said to be characterized by good polishability and good mechanical properties and have a smoothness and transparency corresponding to the natural tooth.

U.S. Pat. Publ. No. 2013/0005846 to Yamazaki et al. discloses an organic/inorganic composite filler that contains: inorganic agglomerated particles comprising agglomerations of inorganic primary particles having a mean diameter between 10 and 1000 nm; an organic resin phase that covers the surface of each inorganic primary particle and binds the inorganic primary particles to each other; and intra-agglomerate voids, formed between the organic resin phase covering the surface of each inorganic primary particle, with a pore volume (here, pore refers to holes with diameters between 1 and 500 nm) between 0.01 and 0.30 $cm^3/g$ as measured by mercury intrusion porosimetry. There is a problem, however, in that Yamazaki et al. is directed toward bonding or gluing together discreet primary particles with a polymer phase and does not provide high transparency filler materials.

WO2015034881A1 to Bringley et al. discloses composite fillers that can be loaded at very high weight or volume fractions without negatively impacting viscosity, and that reduce the volume contraction or shrinkage of the composite. It further discloses composite fillers that are index-matched to the monomers or resins into which they are placed, thereby increasing the transparency and aesthetic qualities of the composite and uniquely allows for preparation of fillers with very high radiopacity. Still further, Bringley et al discloses porous, mixed particle inorganic filler materials that are sintered together to form an extensive network of strong inorganic bonds, thus greatly improving filler strength. The composite filler does not require pulverization or grinding and can be used directly in composite formulations. There is a problem, however, in that the fillers do not provide high-gloss and polish retention, and Bringley et al. fails to provide a method for achieving high translucency both before and after cure.

BRIEF DESCRIPTION OF THE DRAWINGS

FIG. 1 contains the full data table, Table 1, from which excerpts are utilized in the Example section of the specification to facilitate understanding.

PROBLEM TO BE SOLVED

There is a problem in that the fillers of the prior art cannot meet all of the requirements of high strength, low surface area and high loading capacity, low shrinkage, high radiopacity, excellent gloss and wear abrasion, index matching for aesthetic properties, and the elimination of post-processing steps, such as grinding. There is a problem associated with the prior art in that the composite fillers are prepared with a relatively large amount of polymerized organic binder, usually in the range of 20-30 weight %. This limits the hardness and strength that can be achieved. There is a further problem in that the pre-polymerization essentially glues, or binds, the particles together into a mass that must then be pulverized and ground into a filler of smaller grain size. This step is time consuming and costly and further degrades the mechanical and aesthetic properties of the composites. Still further, it creates very small particles, often called fines, which increase the viscosity of the mixtures with monomers and limit the loading of the inorganic component. There is a further problem in that the composite fillers contain air pockets or voids that degrade the optical and aesthetic properties of the fillers. There are additional problems in that the inorganic components of the composite fillers are not precisely matched in refractive index with the organic portion, increasing the visual opacity and degrading the aesthetic quality of the restoration.

There is a need for fillers that may be used in dentistry to reduce shrinkage, that allow very high inorganic loading contents without causing a steep rise in viscosity, and good handling and sculpting properties. There is a need for fillers that do not require costly grinding procedures and that have adequate strength, hardness and aesthetic qualities. There is a need for composites with exceptional gloss and gloss retention after abrasion. There is a need for composites that have high translucency both before and after cure.

SUMMARY OF THE INVENTION

A composite filler comprising thermally processed porous inorganic mixed particles of silica and at least one heteroparticle selected from the group consisting of zirconia, hafnia, or yttria, wherein the porous inorganic mixed particles are thermally processed at a temperature of from 650 to 900° C., and a polymer occupying the pores of the thermally processed porous inorganic mixed particles. The present invention also relates to a dental restorative comprising a resin and a composite filler, and optionally other fillers, wherein said resin has a refractive index that increases upon curing, and wherein the opacities of the both uncured and cured restorative are less than 45.

Advantageous Effect of the Invention

Embodiments of the present invention include several advantages, not all of which are incorporated in a single embodiment. The various embodiments of the invention provide composite fillers that can be loaded at very high weight or volume fractions without negatively impacting viscosity, and reduce the volume contraction or shrinkage of the composite, but also have excellent gloss and gloss retention after abrasion. Surprisingly, it is found that by controlling the primary particle size, sintering and secondary particle size of the fillers, composites can be obtained that, simultaneously, have high loading capacity, excellent viscosity and handling, high mechanical strength, good aesthetics, high-gloss and gloss retention and have translucency that is substantially the same both before and after cure.

DETAILED DESCRIPTION OF THE INVENTION

The present invention relates to a composite filler comprising thermally processed porous inorganic mixed particles of silica and at least one heteroparticle selected from the group consisting of zirconia, hafnia, or yttria and a polymer occupying the pores of the porous inorganic mixed particles, wherein the porous inorganic mixed particles are thermally processed at a temperature of from 650 to 900° C. to obtain a composite filler with excellent properties, especially including high gloss retention. Other factors may be included to further enhance the properties, such as the particle size of the composite filler, the mean particle diameter of the silica and the proximity of the refractive index (RI) of the infused resin to the RI of the porous inorganic particle.

Terms and Definitions

Median particle diameter or median diameter, as used herein, refers to the volume-weighted, median particle diameter.

Heteroaggregate, as used herein, refers to a heterocoagulate that has been heated at a temperature sufficient to form strong chemical bonds between the distinct colloidal particles, fusing them together, usually at a temperature of greater than 600° C. In the present invention, the porous inorganic mixed particle is a heteroaggregate.

Primary particle diameter or median primary particle diameter as used herein refers to the median particle diameter of the colloids, also referred to as heteroparticles, used to prepare the heteroaggregate, also referred to as the porous inorganic mixed particle.

Secondary particle diameter, median secondary diameter, or median secondary particle diameter as used herein refers to the median particle diameter of the heteroaggregate.

Composite Filler, as used herein, refers to fillers comprising both an inorganic and an organic portion.

Composite, as used herein, refers to a polymer or prepolymer that contains at least one inorganic filler, including a composite filler.

Resin, as used herein, refers to a polymerizable mixture of monomers, oligomers or other polymerizable molecules.

Composite Fillers for use in the present invention may be prepared by infiltrating a variety of different resins or resin mixture with different strength, functional groups, surface energy, refractive index, etc.

The inorganic mixed particle materials of the invention are porous and contain micropores or microchannels that are substantially open. Porous inorganic filler materials for use in dentistry have been previously described by Mabie et al., U.S. Pat. Nos. 4,217,264 and 4,306,913 and Randklev, U.S. Pat. No. 4,503,169. These materials of the prior art are typically produced by sintering the component oxides and/or non-oxides at high temperature (700-1100° C.). The sintering temperature is typically chosen such that it is below the melting temperature of any component of the mixture. Extensive melting of the components should be avoided since it may lead to particles that are non-porous.

The preferred porous inorganic particles are mixed particles, or heteroaggregates, and comprise silica and at least one particle selected from the group consisting of yttria, zirconia, and hafnia. Heteroaggregates suitable for use in the invention are described in U.S. Pat. No. 8,617,306 to Lambert et al. and in Bringley et al. U.S. Pat. No. 9,017,733B2, each incorporated herein by reference. Other heteroaggregates useful for the invention comprise silica and at least one oxide selected from the group consisting of alumina, zinc oxide, titania, zirconia, yttria and rare earth oxides. These oxides are preferred because of their unique refractive indices and also because of their significant radiopacity. Also preferred are heteroaggregates comprising at least one oxide and a non-oxide filler selected from hydroxyapatite, fluoro-apatite and alkaline earth fluorides. These non-oxide fillers are preferred because they contain calcium, phosphate and fluoride, all of which are known to promote dental health. Non-preferred materials are non-porous fillers such as those derived from melting process such as glasses, and discreet nanoparticle fillers that are substantially fully densified, although it is possible to use such materials as a minor component of the composite filler.

The porous inorganic particles have a median secondary diameter of less than 5 microns, more preferably from 2 to 4 microns and most preferably from 2 to 3 microns. These particle size ranges are preferred in dentistry because they produce composites that have good mechanical properties while also having good wear/abrasion and gloss properties. In the practice of the invention, it is possible to use other particles as fillers in relatively small proportions including fumed-silica, barium or strontium glass, colloidal and precipitated silica fillers, and radiopaque fillers.

The porous inorganic particle materials of the invention are most preferably produced by the heterocoagulation of colloids. The colloids used for preparing the porous inorganic particles of the invention are preferably selected from aqueous dispersible metal oxide particles including silica, alumina, zirconia, titania, zinc oxide, hafnia, yttria and rare earth oxides. Most preferably, the colloids are silica, alumina, titania, zirconia, or combinations thereof. Specific examples include colloidal, precipitated or fumed silica, aluminas, such as $Al_2O_3$ and its polymorphs, AlOOH (also known as boehmite), zirconia, $ZrO_2$ or hydrous zirconia's, rare earth oxides, such as $Y_2O_3$ and $Yb_2O_3$, and the basic carbonates and nitrates of the aforementioned materials. It is possible to include also other metal oxides, finely ground glasses, and/or metal compounds, such as hydroxides, carbonates, halides, phosphates, nitrates, and the like. Preferred particles that are glasses include barium and strontium glasses although, as mentioned above, they should be used only as a minor component.

The preferred silica particles are colloidal, precipitated or fumed silica's having the general formula $SiO_2$. Silica is used in combination with a second colloid to produce a porous mixed oxide inorganic material. This is preferred, because it allows the refractive index of the composition to be modulated. It is preferred that the silica colloids have a particle size of less than 100 nm, and more preferably from about 20 to 80 nm. In a particular embodiment, it is most preferred that the silica particles are selected from a mixture comprising silica colloids having median primary particle diameter of 20 and 80 nm. Surprisingly, mixtures of silica colloids of these primary particle sizes have exceptional gloss and gloss stability after abrasion. It is preferred that the mixture contains at least 20 weight % of each type of primary particle.

The heteroparticles of the invention comprise crystalline or amorphous inclusions within the porous inorganic particles and have a median primary particle diameter of less than 20 nm. This is preferred, because colloids of these dimensions can be mixed to produce the mixed nanoparticle aggregates whose refractive index can be modulated predictably, based upon the index-weighted, volume fractions of the component nanoparticles.

The colloidal particles before heterocoagulation are preferably stable aqueous colloids. A stable aqueous colloid is one that does not settle or separate from aqueous dispersion for a period of at least one month or more. It is preferred that the stable aqueous colloids have a mean particle diameter of between about 1 and 100 nm, more preferably between 1 and 50 nm and most preferred between 1 and 25 nm.

The median particle diameters of the composite fillers or the porous inorganic particles of the invention may be characterized by a number of methods, or combination of methods, including coulter methods, light scattering methods, sedimentation methods, optical microscopy and electron microscopy. Light scattering methods sample a billion or more particles and are capable of giving excellent particle statistics.

Light scattering methods may be used to give the percentage of particles existing within a given interval of diameter or size, for example, 90% of the particles are below a given value. Light scattering methods can be used to obtain information regarding mean particle size diameter, the median particle diameter, the mean number distribution of particles, the mean volume distribution of particles, standard deviation of the distribution(s) and the distribution width for the particles.

In practice of the invention, it is preferred that the particle size is expressed as the median, volume-weighted particle size. This is the value (in microns) at which, by volume, half of the particles are larger and half are smaller.

The heterocoagulation may be accomplished by mixing the selected colloids and calcium or phosphorus sources, such as phosphates, in a suitable dispersion medium. The preferred dispersion medium is water. The mixing may be accomplished by using a suitable mixing apparatus, such as a blade or prop-like stirrer, a magnetic stirrer, a static mixer, in-line mixers, dispersators, or other high shear mixing apparatus. The mixing efficiency of the apparatus is dependent upon the type of mixing method chosen and the precise geometry and design of the mixer. Complete mixing of the two, or more solutions is preferably accomplished in less than about 10 seconds, and is more preferably accomplished substantially instantaneously.

After heterocoagulation of the particles, a porous inorganic material with a given refractive index is produced by drying and thermal processing to produce a sintered heteroaggregate. The drying and/or thermal processing may be accomplished in separate steps, or combined into a single step. It is most preferred that the dried heterocoagulated mixed particles are thermally processed at a temperature below the melting point of the mixture, or at least below the melting point of the main component of the mixture. The thermal processing step increases the homogeneity of the mixture, decreases the apparent surface area, and importantly, increases the strength of the heteroaggregate. Generally, higher thermal processing temperatures provide stronger materials that have lower surface areas. However, there is a problem in that if the temperature is too high it may produce melted aggregates that may have poor abrasion and gloss properties when employed in composites. This is because the hard aggregates may pluck out from the surface of the composite leaving behind large voids.

Alternatively, lower thermal processing temperatures lead to materials with extremely high surface area and poor strength. The precise thermal processing characteristics are therefore important to tune the properties of the composite. It is preferred that the thermal processing temperature is between about 650 to 900° C., and more preferably from about 700-875° C. Surprisingly, it has been found that composite fillers that are prepared from porous inorganic particles that are sintered or thermally processed at the preferred temperatures have excellent wear, gloss and gloss retention after abrasion.

During the thermal processing step, the particle components fuse together to form strong, micron-sized heteroaggregates that consist of many millions of partially fused nanoparticles. This reduces the surface area of the particles and increases their strength. It is preferred that the heteroaggregates, after thermal processing, have a specific surface area between about 5-200 m²/g and it is more preferred that the surface area is controlled to be from about 10-100 m²/g. It is still more preferred that the surface area is controlled to be from about 40-70 m²/g. The reduction in surface area facilitates the integration of the materials of the invention into polymers, monomers, composites and other formulations, and also increases the mechanical strength of the composites made therefrom. It is further important that the surface area is not reduced to below about 5 m²/g, since low surface area materials have little porosity and limit the amount of polymer that can be infused within the pores.

After thermal processing, the porous inorganic particles contain crystalline and/or amorphous microdomains or regions. It is preferred that porous inorganic particles contain at least one crystalline or semicrystalline phase. It is also highly preferred that the crystalline or semicrystalline phases have microdomains less than about 50 nm and more preferably less than about 20 nm. The inclusion of such microdomains of crystalline or semicrystalline phases allows the refractive index of the porous inorganic particles to be tuned to a given value. The smaller the amorphous, crystalline or semicrystalline inclusions, the less scatter of visible light, which allows the refractive index to be tuned to a precise value. Materials of known and narrow refractive index dispersion are particularly useful in optical applications and in applications where the aesthetic quality of a device, item or article is prized. It is preferred that the refractive index of the porous inorganic particles is between about 1.48 and 1.58, most preferably from 1.52 to 1.58. These ranges encompass the refractive index range for a wide variety of polymers and monomers that are useful in optical, medical and coating applications.

The porous inorganic particles of the invention are sintered, also referred to as thermally processed, to produce strong, micron-sized particles that are porous. It is preferred that the porosity is produced by high temperature thermal processing, and not by other methods that produce only relatively weak particles. The strength of the sintered particles of the invention is demonstrated by the fact that, regardless of the particle size of the colloids used in preparation, the porous inorganic particles are micron-sized and cannot be diminished back into primary particles, even with extensive milling or grinding. The porosity serves several functions including improving abrasion and wear resistance of the particles. Porous particles have improved abrasion and wear since they may shear particle-by-particle at the surface of a coating, whereas nonporous materials may pluck out leaving behind a void. The pores create internal surface, which may soak up monomer(s) by capillary force and exclude monomer from the external surfaces of the particle. The pores are substantially open and accessible by diffusion to small molecules and/or oligomers. It is preferred that the porous inorganic particles are substantially free of closed pores since closed pores are not accessible by diffusion and thus prevent polymerization within the pores, and because closed pores reduce transparency. It is preferred that the pores constitute approximately 10-70%, and more preferably 25-50% of the volume of the particle.

In the practice of the invention, an organic material, typically a pre-polymer, is infused within the pores of the porous inorganic material and polymerized therein to produce a composite filler. The pores are infused with monomers, oligomers and/or polymer precursors (collectively referred to as resins) that are subsequently polymerized within the pores, such that the pores are substantially filled with polymer.

It is preferred that the composite filler is at least 70 percent by weight, preferably 80 percent by weight, and more preferably greater than 84% by weight, porous inorganic particles. Conversely, it is preferred that the polymer occupying the pores of the porous inorganic particles comprises a weight percent from about 8 to 16%. In practice of the invention it is important to match, as best as possible, the polymer volume with the pore volume. This insures that the majority of the resin, and after polymerization the polymer, is absorbed within the pores. Excessive polymer concentrations may lead to bonding or gluing of particles together, thus necessitating milling or grinding steps to diminish the particle size. It is preferred that the median secondary particle diameter of the composite filler, after polymerization, is not greater than 2-times the median secondary particle diameter of the porous particles.

The composite filler of the invention has low surface area and therefore can be loaded at very high solids concentrations within resins. The low surface area is brought about by filling the pores of the porous inorganic particles with polymer. It is preferred that all of the pores in the composite filler are completely filled and the composite filler is substantially free of voids.

Resins containing the composite filler, when cured, produce composites with high strength, gloss, wear and abrasion characteristics, and low curing shrinkage. Most importantly, the composite filler, when properly matched to a resin system, and/or a cured resin system (i.e., a polymer), may produce composites that have exceptional aesthetic qualities such as high transparency and translucency. The transparency of a composite or article can be measured in a variety of ways, the most common of which is the fluid immersion method wherein a filler is dispersed within fluids of known refractive index and relative light transmission of the resulting dispersion is measured. The maximum light transmission corresponds to a matching of the refractive index between the filler and the fluid, and so provides a method for determining the refractive index of the filler. This provides the maximum transparency when, in practice, the composite fillers are dispersed within a resin and the resin cured to produce an article.

In a simple form, transparency refers to the ability to see through an object (such as the case for a window) and to recognize and discern objects on the other side. The transparency of articles prepared using the inventive compositions will be dependent upon the precise index match, the loading of the composition within the resin, and the thickness of the article produced. Herein, the transparency is measured by way of a Transparency Index, described in the Description of Testing Materials: Optical Measurements in the Experimental section, wherein higher index indicates greater transparency. Transparency indices of 12 or greater indicate transparencies approaching window glass, whereas an index of about 8-11 represents a slightly scattering (translucent) medium, and indices of 7 and below indicate increasingly opaque materials. It is preferred that the transparency of the composite filler is greater than 8, it is more preferred that it is greater than 10.

Management of Refractive Index.

In practice of the invention, the actual choice of resins and refractive indices for all components is quite complex. The complexity arises from the fact that, although most resin systems have a refractive index between about 1.44 and 1.60, their refractive index typically increases upon polymerization, usually by about 0.02-0.03 units. In the invention, it is preferred that both the porous inorganic particles and the composite filler, have a refractive index between 1.48 and 1.58, more preferably between 1.52 and 1.58.

However, in practice of the invention, it is possible to tune or adjust the refractive index of the composite filler, by proper choice of the components. When the porous inorganic particles are infused with a polymer having a lower refractive index, the refractive index of the corresponding composite filler is reduced. Accordingly, when the porous inorganic particles are infused with a polymer having a higher refractive index, the refractive index of the corresponding composite filler is increased. In order to facilitate the adjustment of refractive index, it is preferred that the difference between the refractive indices of the polymer and the porous inorganic particles is greater than 0.015.

Shade Matching the Restoration Before and after Cure.

In a preferred embodiment, the composite fillers of the invention are employed in dental restorations. The object of dental restorations is to re-construct teeth to their original form, function and appearance, for example, after caries or trauma to the jaw. There are multiple challenges in restorative dental technology, as the dentist must apply, form and sculpt a restoration that matches tooth form, function (strength), shade and appearance. In practice, after the restoration is prepared, it is cured in place by using a high-energy light-wand in the blue or UV range of the light spectrum. There is a problem that arises as a result of the fact that the refractive index of the resin changes during curing. It is essential that the restoration be translucent to the curing radiation, so that the light may penetrate deeply and properly cure the inner portion (i.e., the backside adjacent to the remaining tooth structure). However, because the refractive index of the resin portion changes during curing, the optical or aesthetic appearance of the restoration also changes, and can lead to a shift in color of the restorations such that it no longer matches the adjacent natural teeth. This is especially true if the opacity (i.e., the opposite of transparency) of the restoration changes significantly during cure. In the prior art, it is most typically practiced that the filler and resin (before polymerization) comprising the composite have the same refractive index. Therefore, the optical properties of the composite change during curing, potentially leading to a color shift. The authors of the present invention have discovered, surprisingly, that if the polymerized resin portion of the composite filler has a refractive index that is significantly greater than the filler, it shifts the effective refractive index of the composite filler to a higher value. Further, it is discovered that dental composites prepared from such composite fillers have optical properties that are closely matched before and after cure, and avoid the shade mismatch dilemma discussed above.

The invention described herein solves this problem as it provides a dental restorative comprising a resin and a composite filler, and optionally other fillers, wherein the resin has a refractive index that increases upon curing, and wherein the opacities of the both uncured and cured restorative are less than 45. Low opacity values are preferred because they provide for good optical translucency, affording restorations with luster and optical brilliance; and also because they have good light penetration ensuring that the restoration is adequately cured. It is further preferred that the opacity, both before and after cure, is less than 40. It is preferred that the difference between the uncured and cured opacities is less than 15. This is preferred because it minimizes color shift of the restoration during curing.

In practice of the invention, the restorative must be strong and durable. The human oral cavity is an extremely challenging environment as it is constantly wet, subject to debris and bacteria, and subject to mastication forces over many decades. To increase strength and durability it is preferred that the composite filler contains at least one monomer that is a trifunctional, tetrafunctional or a greater functional monomer. This is preferred because it allows for greater cross-linking or "anchoring" of the composite filler into the dental restorative during cure.

In order to facilitate the integration of the compositions of the invention into polymers, monomers, composites or other formulations, it may be necessary to functionalize the surfaces of the porous inorganic particles with surface agents, for example, surfactants, coating aids, coupling agents, or the like. This step may be accomplished before, or after, the infusion and polymerization processes. It is preferred that it is done before the infusion and polymerization process. It is preferred that the particles have their surfaces functionalized by silane coupling agents, or hydrolyzed precursors of silane coupling agents having the general formula:

$$R_a R'_b Si(OR'')_{4-(a+b)},$$

where a and b are integers from 1 to 3, (a+b) is less than or equal to 3, R and R' are organic groups having from 1-30 carbon atoms and R'' is H, or an organic group having from 1 to 6 carbon atoms.

Alternatively, the silane coupling agent may have the general formula:

$$R_a Si(X)_{4-a},$$

where a and R is as defined above and X is a halogen, Cl, Br or I.

Specific examples of silane coupling agents useful for practice of the invention include but are not limited to 3-mercaptopropyl(trimethoxy)silane, 3-mercaptopropylmethyl(diethoxy)silane, methacryloxypropyl(trimethoxy)silane, 2-[methoxy(polyethyleneoxy)propyl](trichloro)silane, 2-[methoxy(polyethyleneoxy)propyl](trimethoxy)silane, octyl(trimethoxy)silane, octadecyl(trimethoxy)silane, 3-isocyanatopropyldimethylchlorosilane, 3-isocyanatopropyl(triethoxy)silane, Bis(2-hydroxyethyl)-3-aminopropyltriethoxysilane, aminopropylsilanetriol, 3-aminopropyl(triethoxy)silane, 3-aminopropyl(trimethoxy)silane, N-(2-aminoethyl)-3-aminopropylsilanetriol, N-(2-aminoethyl)-3-aminopropyl(trimethoxy)silane, N-(2-aminoethyl)-3-aminopropylmethyldimethoxysilane, isopropyl(trimethoxy)silane, (3-glycidoxypropyl)methyldimethoxysilane, tetradecyldimethyl(3-trimethoxysilylpropyl)ammonium chloride, (3-trimethoxysilylpropyl)diethylenetriamine and octadecyldimethyl(3-ammonium)propyl(trimethoxy)silane.

To initiate the surface reaction, the particles and the surface agent(s) are mixed together in a high shear mixing zone within a dispersion medium. It is preferred that the dispersion medium is water, but other solvents or liquids may also be used.

In the preparation of the composite filler of the invention, the porous inorganic nanoparticle material is mixed with a resin or pre-polymer, usually within a solvent or medium in which the resin is soluble. Suitable media are any liquid in which the resin or pre-polymer is soluble, but preferred media are water and or organic solvent, such as acetone, methanol, ethanol, isopropanol, ether or other volatile organic solvents. A polymerization initiator and/or accelerator is then added to the mixture. Initiators and accelerates generally initiate polymerization only after a stimulus is applied such as heat, light or other radiation. After the mixture is homogeneously mixed, the solvent is then removed by vacuum distillation, or another evaporative process. This reduces the mixture to a free flowing powder.

The resin or pre-polymer portion of the powder is then polymerized by application of light, heat or other known means to initiate polymerization. It is preferred that the organic resin or pre-polymer material is polymerized substantially within the pores and not on the surface, or outside of, the porous inorganic nanoparticle material. Although some polymerization outside of the pores is difficult, if not impossible in practice to prevent, surprisingly, at the appropriate loadings, substantially all of the resin is polymerized within the pores. In another embodiment of the invention, the composite filler particles of the invention are dispersed within a matrix.

The matrix may comprise at least one fluid, polymer, oligomer, monomer or combinations thereof. It is preferred that the inventive compositions are dispersed within the polymer, oligomer, or monomer matrix at a loading of 1-80% by weight. It is preferred that the polymer, oligomer and/or monomer(s) are thermal or light curable. Useful examples of polymers for the matrix are acrylate-functional materials, methacrylate-functional materials, epoxy-functional materials, vinyl-functional materials, and mixtures thereof. Typically, the hardenable resin is made from one or more matrix forming oligomers, monomers, polymers, or blend thereof. Also useful are urethanes, fluoropolymers, siloxanes and latex polymers.

In certain embodiments, the inventive materials are used in dental applications or in orthopedic, or other in vivo, applications. It is preferred that the composite filler is a dental composite filler. It is preferred that the composite is dispersed in a light polymerizable resin matrix. Polymerizable matrix materials suitable for use in these applications include hardenable organic materials having sufficient strength, hydrolytic stability, and nontoxicity to render them suitable for use in the oral or in vivo environment. Examples of such materials include acrylates, methacrylates, urethanes, carbamoylisocyanurates, epoxies, and mixtures and derivatives thereof. One class of preferred hardenable materials includes materials having polymerizable components with free radically active functional groups. Examples of such materials include monomers having one or more ethylenically unsaturated group, oligomers having one or more ethylenically unsaturated group, polymers having one or more ethylenically unsaturated group, and combinations thereof.

In the class of hardenable matrix resins having free radically active functional groups, suitable polymerizable components for use in the invention contain at least one ethylenically unsaturated bond, and are capable of undergoing addition polymerization. Such free radically ethylenically unsaturated compounds include, for example, mono-, di- or poly-(meth)acrylates (i.e., acrylates and methacrylates), such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis [1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, and trishydroxyethyl-isocyanurate trimethacrylate; (meth)acrylamides (i.e., acrylamides and methacrylamides), such as (meth)acrylamide, methylene bis-(meth)acrylamide, and diacetone (meth)acrylamide; urethane (meth)acrylates and the bis-(meth)acrylates of polyethylene glycols. Other suitable free radically polymerizable compounds include siloxane-functional (meth)acrylates and fluoropolymer functional (meth)acrylates. Mixtures of two or more free radically polymerizable compounds can be used, if desired.

Examples of other useful matrix polymers include natural and synthetic biopolymers, such as peptides, proteins, gelatin, poly(lactic acid), poly(glycolic acid), poly(caprolactone), chitosan and its derivatives, alginates and the like.

EXAMPLES

The following examples are provided to illustrate the invention.

Materials

All material concentrations are given as weight to weight percentages unless otherwise noted.

NALCO 2327® is a colloidal dispersion of silica in water, the mean silica particle diameter is 20 nm and the solids concentration 40.0%.

NALCO 2329® is a colloidal dispersion of silica in water, the mean silica particle diameter is 75-100 nm and the solids concentration 40.0%.

NALCO DVSN004® is a colloidal dispersion of silica in water, the mean silica particle diameter is 40 nm and the solids concentration 40.0%.

Zirconyl Acetate® is a colloidal zirconia dispersion sold by Nyacol Nanotechnologies with a mean particle diameter of 5-10 nm.

2,2'-Azobis(2-methylpropionitrile) (AIBN) is a thermal polymerization initiator purchased from Aldrich Chemical Company.

SR541, SR238B, SR351, hexanediol diacrylate, Trimethylolpropane triacrylate, urethane dimethacrylate (UDMA), SR101 and triethylene glycol dimethacrylate (TEGDMA) are polymerizable methacrylate and acrylate monomers purchased from Sartomer USA, LLC.

Ethoxylated Bis Phenol A Dimethacrylate (EBPADMA) was purchased from Esstech Inc.

Resin mixture A consisted of a mixture of the monomers SR541, EBPADMA, SR238B and SR351 in a weight ratio of 50:20:15:15, respectively. The calculated refractive index of the resin mixture was 1.507; polymerized Resin mixture A has a refractive index of 1.532).

Description of Testing Methods.
Calculation of Refractive Indices.

Refractive indices ($\eta_{tot}$) were estimated for all compositions using the relationship given in equation 1.

$$\eta_{tot} = (n_1 V_1 + n_2 V_2 + n_3 V_3)/V_{tot} \quad (1)$$

where $\eta_1$, $\eta_2$ and $\eta_3$ are the refractive indices of the individual components and $V_1$, $V_2$ and $V_3$ are the respective volume fractions of that component. The refractive indices used were the reported values; (1.46 for $SiO_2$, 1.675 and 2.115 for zirconia). The volumes for each phase are calculated based on the weight percentages and densities of the components. Monomer indices and densities were taken from the manufacturers published literature. For polymerized samples, the polymer index is estimated to increase by 0.025 units from that of the resin system; this increase is consistent with reported literature values for dental resins.

Optical Measurements

The refractive index match and relative transparency in dental monomers was determined by making mixtures of the mixed oxide in a monomer of known refractive index at 35 wt. %. The monomers were purchased from Sartomer Chemical or Esstech Inc. and are methacrylate monomers commonly used in dental restoratives. The mixtures were sonicated to remove air bubbles, and 3.08 g of the mixtures were added into a glass vials to a depth of about 7.0 mm. The mixtures were placed on a light box and a series of optical targets were viewed by looking through the thickness of the sample. The mixtures were given a relative transparency score corresponding to the smallest font feature discernable (clearly visible and readable). Font sizes varied from 26-point to 2-point. For example, a rating of 1 indicates that only a 26-point font is readable, a score of 5 refers to readability of 18-point font or larger, 10=8-point and 13=2-point or larger. This simple qualitative method of determining transparency has an estimated accuracy of ± a score of 0.5. This method of ranking the relative transparency of the mixtures was validated using transmission spectrophotometry. The mixtures described above were measured on a Perkin Elmer Lambda 20 spectrometer at a thickness of 1.0 mm in a borosilicate glass slide cell (empty cell used as reference). Transparency was determined as the mean % transmission between 500 to 600 nm. Samples were approximately 1 cm from the detector. Refractive indices of the powders were approximated by placing the powders in a series of fluids of known refractive index and noting the highest transparency.

General Procedure for Producing Composite Fillers:
Preparation of Composite Filler (C1):

Into a 20 L reactor containing 2,076.1 g of zirconyl acetate (Nyacol Nanotechnologies, 20.0% zirconia solids) that was stirred with a prop-like mixer spinning at 2000 rpm, was added 4,104.6 g of colloidal silica (NALCO 2327; 40.0% silica solids) at a rate of 90.0 g/min. After addition, the reaction mixture was allowed to stir for 1 hour. After preparation, the product was dried in a forced air oven at 110° C. The solid obtained was milled with 9 mm alumina beads for 3 hours and the resulting fine powder was fired in a programmable furnace at 966° C. for 3 hours and allowed to cool. To 450.0 g of the filler thus obtained was added 400.0 g acetone, 27.0 g of gamma-methacryloxypropyl (trimethoxy)silane and 8.1 g 0.1 N acetic acid and the contents stirred for 16 hours. After this time was added 74.25 g of resin mixture A and 0.74 g of AIBN. The solvent was then removed under vacuum at 45° C. and the resin was polymerized by heating the powder at 110° C. for 4 hours under nitrogen gas. This procedure yielded a composite that contained 14.2% polymer by weight and a mean particle diameter of 6.0 microns. The corresponding fillers of the invention were prepared by modification of this general procedure including silica colloid primary particle diameter, milling time, firing temperature, polymer weight percent and final median particle diameter as indicated in Table 1.

Procedure for Producing Composite Filler Used in Example 12.

The composite filler used in Example 12 was prepared identically to that of Example 3, except that Resin 1 (refractive index 1.525; polymerized refractive index 1.550) was substituted for resin mixture A.

Preparation and Evaluation of Composites.

Composite examples, including one comparative sample (C1) and 11 test samples, were prepared to illustrate the benefits of including Composite Fillers described above in dental composites compromising a light-curable resin base material that include commercially available monomers containing methacrylate groups and a hydrophobic fumed-silica, specifically CaboSil TS530 (available commercially from Cabot. Inc.).

TABLE 2

| Resin Composition | | |
|---|---|---|
| | Resin 1 (wt %) | Resin 2 (wt %) |
| BisGMA (Bisphenol A Diglycidyl ether dimethacrylate) | 9.9% | 31.6% |
| Triethylene Glycol Dimethacrylate | 4.9% | 13.7% |
| Ethoxylated Bisphenal A dimethacrylate (no. of ethoxy groups = 3.5) | 24.7% | 27.8% |
| Ethoxylated Bisphenal A dimethacrylate (no. of ethoxy groups = 6) | 59.2% | — |
| Urethane dimethacrylate | — | 25.8% |
| 2-hydroxy-4-methoxybenzophenone | 0.5% | 0.6% |
| BHT (2-hydroxy-4-methoxy Benzophenone butylated hydroxytoluene) | 0.1% | 0.0% |
| Camphorquinone | 0.2% | 0.1% |
| Ethyl-4-dimethylamino benzoate | 0.5% | 0.4% |
| Total | 100% | 100% |
| Refractive Index (before polymerization) | 1.525 | 1.512 |

Table 2 lists the components of the resins that were used for Comparison Example 1 and Examples 2-12.

Comparison Example 1

Twenty-one grams composite filler (C1), whose preparation is given above, and 0.6 g fumed-silica TS530, are added portion by portion to 8.4 g of Resin 1 while mixing with a high speed mixer. After thoroughly mixing, the composite paste was de-aerated under attenuated oxygen pressure.

Examples 2-12

Examples 2-12 were prepared in an identical manner as that of Comparison Example 1, except that the composite filler was modified as given in Table 1, and substituted for composite filler C1.
Composite Test Method
Flexural Strength and Flexural Modulus.

For the three-point flexural strength test, 6 bar-shaped specimens were fabricated from each comparison example or example, according to ISO4049. The composites were packed inside a stainless steel mold (25 mm×2 mm×2 mm) and covered with a piece of mylar sheet to extrude excess materials. The specimens were polymerized for 120 s on each side in a light curing box. Specimens were soaked in water at 37° C. for 24 h and after removed from the mold. Specimens then were tested using a three-point bending device test in a universal testing machine at a crosshead speed of 0.5 mm/min until fracture.
Sample Preparation and Polish.

Composite was first loaded in a stainless steel mold (1.5 mm thick, 3.8 cm in diameter), pressed down with a glass block with Mylar film on top of the composite, and then cured with following steps: Spot cure composite for 60 seconds at each location in overlapping increments. Start in the middle and work the curing light around the middle until the complete composite surface is exposed. Remove the specimen and repeat the light cure on the underside.

The cured composite specimen was polished with 240-grit silicon carbide paper followed by 600-grit on both surfaces. Using a polishing rubber wheel, the specimen was polished in one uniform direction for 60 seconds ensuring the entire surface had been covered, The specimen was rotated 45 degrees and the polish repeated with a rubber wheel until all four directions had been polished. The specimen was then rinsed with water to remove debris. Similar polish steps were performed by replacing the polishing rubber wheel with a Felt wheel (on-layer medium) and polishing paste (Diamond 800_654) first then, same polish steps were followed with Felt wheel (on-layer medium) and polishing paste (Superfine Diamond 800_656), last polish step were done similarly using Felt wheel (three layer medium buffer wheel. After conditioning the specimen in water at 37° C. for seven days, Gloss retention (initial) was measured on the appropriately dried specimen with the BYK Gardner gloss instrument set at 60°. A measurement was performed and the specimen was rotated 45 degrees before taking another measurement. In all, four measurements of gloss were taken at positions 12:00, 3:00, 6:00 and at 9:00 and the average of the four measurements was computed.

Gloss Retention after Toothbrush Wear.

The conditioned polished specimen was fit into a turntable with a reservoir to accommodate a diluted toothpaste slurry. An Oral B electric tooth brush was fitted into another turning fixture with the toothbrush head positioned at the center of the specimen. The specimen on the turn table was rotated at 165 rpm, while the toothbrush moved across 2 cm of the specimen surface in a linear back-forth motion with frequency about 9-lap/minute. A constant hanging weight of 300 g was applied to the tooth brush turning fixture 10 cm away to the center of the turning table to assure good contact between the toothbrush head and the specimen surface.

Meanwhile the toothbrush head vibrated per Oral B electric toothbrush manufacturer specification. Gloss retention of specimen was measured after 1-hour and 2-hour toothbrush wear with the BYK Gardner gloss instrument set at 60° following the same procedure described previously, the average of four gloss values was reported.

The data of Table 1 of FIG. 1 show multiple benefits. The gloss of the dental composites of the invention are dramatically improved over the comparison composite that has a median secondary particle diameter of 6.0 microns, as illustrated by this Excerpt A of Table 1.

| Excerpt A | | | | | | | | | | | | |
|---|---|---|---|---|---|---|---|---|---|---|---|---|
| | C1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 |
| Composite Filler Properties | | | | | | | | | | | | |
| 2° particle diameter (microns) | 6.0 | 4.0 | 2.6 | 2.6 | 3.2 | 4.3 | 4.8 | 4.6 | 3.8 | 3.8 | 3.8 | 2.9 |
| Composite Properties | | | | | | | | | | | | |
| Gloss retention (initial) | 51.8 | 90.3 | 90.6 | 90 | 89.3 | 89.1 | 84.9 | 82.5 | 88.0 | 87.2 | 89.8 | 89.8 |

The data further show that composite fillers prepared at a lower sintering temperature have, quite surprisingly, very significantly improved gloss retention after abrasion, as illustrated by this Excerpt B of Table 1.

| Excerpt B | | | | | | | | | | | | |
|---|---|---|---|---|---|---|---|---|---|---|---|---|
| | C1 | Ex. 2 | Ex. 4 | Ex. 3 | Ex. 5 | Ex. 6 | Ex. 7 | Ex. 8 | Ex. 9 | Ex. 10 | Ex. 11 | Ex. 12 |
| Composite Filler Properties | | | | | | | | | | | | |
| Firing Temperature, ° C. | 966 | 966 | 966 | 866 | 866 | 766 | 816 | 866 | 766 | 816 | 866 | 866 |
| Composite | | | | | | | | | | | | |

-continued

Excerpt B

|  | C1 | Ex. 2 | Ex. 4 | Ex. 3 | Ex. 5 | Ex. 6 | Ex. 7 | Ex. 8 | Ex. 9 | Ex. 10 | Ex. 11 | Ex. 12 |
|---|---|---|---|---|---|---|---|---|---|---|---|---|
| Properties |  |  |  |  |  |  |  |  |  |  |  |  |
| Gloss retention (initial) | 51.8 | 90.3 | 90 | 90.6 | 89.3 | 89.1 | 84.9 | 82.5 | 88.0 | 87.2 | 89.8 | 89.8 |
| Gloss retention (after 1 h) | 45.8 | 54.2 | 50.8 | 73.7 | 61.9 | 83.1 | 81.2 | 79.7 | 80.7 | 78.1 | 71.2 | 71.2 |
| Gloss retention (after 4 h) | 45.3 | 57.5 | 59.9 | 74.8 | 70.3 | 82.7 | 80.9 | 82.1 | 78.6 | 79.7 | 70.9 | 70.9 |

The data of Table 1 also show that gloss retention improves with increasing silica primary particle diameter, as illustrated by this Excerpt C of Table 1. This is an important result since larger primary particles have lower surface area and allow the dental composite formulator greater freedom in adapting the paste viscosity.

Excerpt C

|  | Ex. 6 | Ex. 7 | Ex. 8 | Ex. 9 | Ex. 10 | Ex. 11 |
|---|---|---|---|---|---|---|
| Composite Filler Properties |  |  |  |  |  |  |
| Silica 1° particle diameter (nm) | 80 | 80 | 80 | 20 & 80* | 20 & 80* | 20 & 80* |
| Composite Properties |  |  |  |  |  |  |
| Gloss retention (initial) | 89.1 | 84.9 | 82.5 | 88.0 | 87.2 | 89.8 |
| Gloss retention (after 1 h) | 83.1 | 81.2 | 79.7 | 80.7 | 78.1 | 71.2 |
| Gloss retention (after 4 h) | 82.7 | 80.9 | 82.1 | 78.6 | 79.7 | 70.9 |

*Silica primary particles were chosen from Nalco 2327 and Nalco 2329 at a 50:50 weight ratio.

Further the data of Table 1 show that if the resin that comprises the organic portion (polymer) has a refractive index that is close to that of the porous inorganic particles, then the opacity of the resulting composite is low. A low opacity is advantageous since it gives the tooth restoration translucency and optical brilliance and allows the dentist to better match natural tooth appearance and shade. Still further, the opacity remains about the same both before and after cure, and therefore avoids changes in shade and appearance after the tooth restoration is fully cured, as illustrated by this Excerpt D of Table 1.

Excerpt D

|  | C1 | Ex. 3 | Ex. 12 |
|---|---|---|---|
| Composite Filler Properties |  |  |  |
| Firing Temperature, °C. | 966 | 866 | 866 |
| RI** porous inorganic particles | 1.523 | 1.523 | 1.523 |
| RI** polymerized organic portion (resin) | 1.532 | 1.532 | 1.550 |

-continued

Excerpt D

|  | C1 | Ex. 3 | Ex. 12 |
|---|---|---|---|
| Composite Properties |  |  |  |
| Opacity (before cure) | 34.5 | 24.4 | 27.8 |
| Opacity (after cure) | 52.6 | 51.0 | 38.9 |

**RI = refractive index

The invention claimed is:

1. A composite composition comprising:
   a composite filler comprising
     thermally processed porous inorganic mixed particles of silica and zirconia, and
     a polymer occupying the pores of the thermally processed porous inorganic mixed particles of silica and zirconia; and
   a resin;
   wherein the composite composition exhibits an average gloss retention after 1 hour of abrasion of at least 61.9 gloss units.

2. The composite composition of claim 1, wherein the silica particles of the composite filler have a median primary particle diameter of less than 100 nm.

3. The composite composition of claim 2, wherein the median primary particle diameter of the silica particles is from 20 nm to 80 nm.

4. The composite composition of claim 1, wherein:
   the silica particles of the composite filler are chosen from a mixture comprising silica colloids of a first type and a second type;
   the first type of the silica colloids has a median primary particle diameter of 20 nm, and is present in the mixture at a concentration of at least 20 weight percent; and
   the second type of the silica colloids has a median primary particle diameter of 80 nm and is present in the mixture at a concentration of at least 20 weight percent.

5. The composite composition of claim 1, wherein the polymer occupying the pores of the thermally processed porous inorganic mixed particles of silica and zirconia is present in the composite filler at a weight percent from 8 to 16.

6. The composite composition of claim 1, wherein the composite filler is substantially free of voids.

7. The composite composition of claim 1, wherein the zirconia is present in the thermally processed porous inorganic mixed particles at a concentration greater than 25% by weight.

8. The composite composition of claim 1, wherein:
the composite filler is at least 84 percent by weight thermally processed porous inorganic particles of silica and zirconia; and
the composite filler has a median secondary particle diameter of not more than 2 times a median secondary particle diameter of the thermally processed porous inorganic particles.

9. The composite composition of claim 1, wherein a refractive index of the thermally processed porous inorganic mixed particles of silica and zirconia is between 1.48 and 1.58.

10. The composite composition of claim 9, wherein the refractive index of the thermally processed porous inorganic mixed particles of silica and zirconia is between 1.52 and 1.58.

11. The composite composition of claim 1 wherein the zirconia has crystalline or amorphous inclusions and a median primary particle diameter of less than 20 nm.

12. The composite composition of claim 1, wherein the thermally processed porous inorganic mixed particles of silica and zirconia have a particle size distribution width of about 4 microns.

13. The composite composition of claim 1, wherein the resin comprises a free radically ethylenically unsaturated compound.

14. The composite composition of claim 1, wherein an average gloss retention of the composite composition after 4 hours of abrasion is at least 70.3 gloss units.

15. The composite composition of claim 1, further comprising fumed silica;
wherein the composite filler, the resin, and the fumed silica are in the composite composition in approximately the proportion 35:14:1.

16. The composite composition of claim 1, wherein the thermally processed porous inorganic mixed particles of silica and zirconia have been thermally processed at a temperature of from 700° C. to 875° C.

17. The composite composition of claim 16, wherein:
the thermally processed porous inorganic mixed particles of silica and zirconia have been thermally processed at a temperature of about 866° C.; and
the thermally processed porous inorganic mixed particles of silica and zirconia have a secondary particle diameter of from 2 microns to 4 microns.

* * * * *